US012753381B2

(12) United States Patent
Liu et al.

(10) Patent No.: US 12,753,381 B2
(45) Date of Patent: Oct. 6, 2026

(54) CELL SEPARATION APPARATUS FOR BIOREACTOR

(71) Applicant: ALIT BIOTECH (SHANGHAI) CO., LTD., Shanghai (CN)

(72) Inventors: Yu Liu, Shanghai (CN); Rui Chen, Shanghai (CN)

(73) Assignee: ALIT BIOTECH (SHANGHAI) CO., LTD., Shanghai (CN)

( * ) Notice: Subject to any disclaimer, the term of this patent is extended or adjusted under 35 U.S.C. 154(b) by 1009 days.

(21) Appl. No.: 17/821,158

(22) Filed: Aug. 19, 2022

(65) Prior Publication Data

US 2023/0159880 A1 May 25, 2023

Related U.S. Application Data

(63) Continuation-in-part of application No. PCT/CN2021/073791, filed on Jan. 26, 2021, and a (Continued)

(30) Foreign Application Priority Data

Feb. 19, 2020 (CN) ......................... 202010101731.0
Jul. 23, 2020 (CN) ......................... 202010717020.6

(51) Int. Cl.
*C12M 1/00* (2006.01)
*B01F 27/192* (2022.01)
(Continued)

(52) U.S. Cl.
CPC ......... *C12M 47/02* (2013.01); *B01F 27/1921* (2022.01); *B01F 27/90* (2022.01);
(Continued)

(58) Field of Classification Search
None
See application file for complete search history.

(56) References Cited

U.S. PATENT DOCUMENTS 4,178,209 A * 12/1979 Tolbert .................. C12M 29/04 435/297.2
4,749,654 A * 6/1988 Karrer .................... C12M 23/24 210/150
(Continued)

FOREIGN PATENT DOCUMENTS

CN 1124292 A 6/1996
CN 2665135 Y 12/2004
(Continued)

OTHER PUBLICATIONS

The Extended European Search Report in European Application No. 21757148.8 mailed on Jun. 30, 2023, 7 pages.
(Continued)

*Primary Examiner* — William H. Beisner
(74) *Attorney, Agent, or Firm* — METIS IP LLC

(57) ABSTRACT

The present disclosure provides a cell separation apparatus for a bioreactor, which comprises: a cell separation component, which is arranged in a tank and immersed below the liquid level of the mixture and includes a filter membrane and a liquid guiding groove; and a tangential flow driving component, which includes one or more blades. The cell separation apparatus implements a low shear force and the filter membrane is not blocked easily. The present disclosure also provides a string system including a central shaft and a multi-layer paddle component. The multi-layer paddle component includes an upper paddle component, an intermediate paddle component and a bottom paddle component arranged around the central shaft.

20 Claims, 10 Drawing Sheets

Related U.S. Application Data continuation-in-part of application No. PCT/CN2021/073802, filed on Jan. 26, 2021.

(51) Int. Cl.

| | |
|---|---|
| ***B01F 27/90*** | (2022.01) |
| ***B01F 27/921*** | (2022.01) |
| ***B01F 101/44*** | (2022.01) |
| ***C12M 1/06*** | (2006.01) |
| ***C12M 1/26*** | (2006.01) |
| ***C12M 1/34*** | (2006.01) |

(52) U.S. Cl.

CPC ......... *B01F 27/9211* (2022.01); *C12M 27/02* (2013.01); *C12M 33/14* (2013.01); *C12M 41/40* (2013.01); *B01F 2101/44* (2022.01)

(56) References Cited

U.S. PATENT DOCUMENTS

| | | | | | |
|---|---|---|---|---|---|
| 4,840,906 | A | | 6/1989 | Kearns et al. | |
| 4,888,294 | A | * | 12/1989 | Van Wezel ............. | C12M 33/10 435/295.3 |
| 4,906,577 | A | * | 3/1990 | Armstrong ............. | C12M 23/38 435/295.3 |
| 4,921,792 | A | * | 5/1990 | Trawinski .............. | C12M 27/02 435/813 |
| 5,019,512 | A | * | 5/1991 | Varecka ................. | C12M 27/20 435/813 |
| 5,126,269 | A | * | 6/1992 | Fike ....................... | C12M 29/10 435/297.3 |
| 8,241,904 | B2 | | 8/2012 | Cheng et al. | |
| 2010/0035343 | A1 | | 2/2010 | Cheng et al. | |
| 2019/0185803 | A1 | | 6/2019 | Grant | |
| 2019/0375661 | A1 | | 12/2019 | Zheng et al. | |

FOREIGN PATENT DOCUMENTS

| | | | |
|---|---|---|---|
| CN | 101851581 | A | 10/2010 |
| CN | 101886038 | A | 11/2010 |
| CN | 102108333 | A | 6/2011 |
| CN | 204125452 | U | 1/2015 |
| CN | 107287100 | A | 10/2017 |
| CN | 107904169 | A | 4/2018 |
| CN | 108004122 | A | 5/2018 |
| CN | 108504575 | A | 9/2018 |
| CN | 208857311 | U | 5/2019 |
| CN | 110479126 | A | 11/2019 |
| CN | 110734847 | A | 1/2020 |
| CN | 210065753 | U | 2/2020 |
| CN | 111117862 | A | 5/2020 |
| CN | 210656875 | U | 6/2020 |
| CN | 111676140 | A | 9/2020 |
| CN | 211972297 | U | 11/2020 |
| CN | 212316142 | U | 1/2021 |
| JP | H0775550 | A | 3/1995 |

OTHER PUBLICATIONS

International Search Report in PCT/CN2021/073791 mailed on Apr. 15, 2021, 7 pages.

Written Opinion in PCT/CN2021/073791 mailed on Apr. 15, 2021, 9 pages.

International Search Report in PCT/CN2021/073802 mailed on Apr. 28, 2021, 6 pages.

The Extended European Search Report in European Application No. 21846360.2 mailed on Sep. 13, 2023, 7 pages.

Yan, Xu et al., Cell Culture of Impeller Suitable for Animals and Its Numerical Simulation, Modern Chemical Industry, 34(10): 162-166, 2014.

Kou, Jie et al., Oilfield Water Treatment, Oilfield Produced Water Treatment, China University of Petroleum Press, 2018, 5 Pages.

Liu, Cheng et al., Membrane Separation Process, Contemporary New Food, Beijing University of Technology Press, 1998, 6 Pages.

Liu, Luoxian et al., Section 5 Other Types of Stirrers, Principle and Equipment of Pharmaceutical Engineering of Traditional Chinese Medicine, China Traditional Chinese Medicine Publishing House, 2007, 7 Pages.

The Second Office Action in Chinese Application No. 202010101731.0 mailed on Mar. 1, 2025, 17 pages.

First Office Action in Chinese Application No. 202010717020.6 mailed on Jul. 31, 2024, 18 pages.

* cited by examiner

CELL SEPARATION APPARATUS FOR BIOREACTOR

CROSS-REFERENCE TO RELATED APPLICATIONS

This application is a continuation-in-part of International Application No. PCT/CN2021/073802, filed on Jan. 26, 2021, which claims priority to Chinese patent application No. 202010717020.6, filed on Jul. 23, 2020. This application is also a continuation-in-part of International Application No. PCT/CN2021/073791, filed on Jan. 26, 2021, which claims priority to Chinese patent application No. 202010101731.0, filed on Feb. 19, 2020. The contents of each of the above-related applications are incorporated herein by reference in their entirety.

TECHNICAL FIELD

The present disclosure involves the field of bioreactors. More specifically, the present disclosure relates to a cell separation apparatus for a bioreactor.

BACKGROUND

In animal cell expansion, more and more processes involve the separation of cells from culture medium or other liquids, comprising perfusion culture, fluid exchange, or cell cleaning. Traditional separation devices include ATF systems and TFF systems. These systems use a diaphragm pump or centrifugal pump as the power to pump the mixture of cells and culture medium into the hollow fiber column, and use the fiber pores of the hollow fiber column to separate cells and culture medium. These systems using a diaphragm pump or centrifugal pump as the power to pump the mixture of cell culture medium have the disadvantage of providing high shear force. Animal cells (especially human T cells or stem cells) are very sensitive to shear force. Excessive shear force may cause tumorigenesis of stem cells or loss of cell logo, which seriously affects the safety of cell therapy products.

Another separation device uses a filtration system floating above the liquid level of the mixture to separate cells from the culture medium. The flow direction of the mixture of the separation device is consistent with the filtration direction of the filter membrane, which is easy to block the filter membrane in the process of use. Filter membrane obstruction often means the failure of the entire process, which not only brings huge economic losses to the enterprise but also delays the precious biological samples and treatment time of patients.

SUMMARY

One object of the present disclosure is to provide a cell separation apparatus capable of overcoming at least one defect in the prior art.

According to all aspects described below, the theme of technology is explained. For convenience, various examples of various aspects of the subject technology are described as numbered clauses (1, 2, 3, etc.). These clauses are provided as examples and do not limit the theme of technology of the present disclosure 1. A cell separation apparatus for a bioreactor, comprising a tank used for containing a mixture of cells and a liquid, wherein the cell separation apparatus comprises: a cell separation component and a tangential flow driving component; wherein the cell separation component is arranged in a tank and immersed below a liquid level of the mixture and include a filter membrane and a liquid guiding groove, wherein the filter membrane is configured to filter the mixture and guide a separated liquid into the liquid guiding groove, the liquid guiding groove comprises a radial outer wall and a radial inner wall, and an internal cavity of the liquid guiding groove is only in fluid communication with the tank through one or more openings on the radial inner wall and through the filter membrane, or only in fluid communication with the tank through one or more openings on the radial outer wall and through the filter membrane; and the tangential flow driving component comprises one or more blades positioned radially inside the cell separation component and capable of rotating about a rotation shaft to drive the mixture to flow tangentially along the filter membrane.

2. The cell separation apparatus according to clause 1, further comprising a liquid collection component arranged outside the tank, the liquid collection component comprising a collection container in fluid communication with the liquid guiding groove, and a collection tube in fluid communication with the collection container and the liquid guiding groove.

4. The cell separation apparatus according to clause 2, wherein a pump is set on the collection tube, and the separated liquid is pumped from the liquid guiding groove to the collection container.

6. The cell separation apparatus according to clause 2, wherein a pressure sensor is set in the collection tube to monitor a liquid pressure in the collection tube.

7. The cell separation apparatus according to clause 1, wherein the cell separation component further comprises a support sheet positioned between the liquid guiding groove and the filter membrane, and the support sheet is configured to support the filter membrane.

10. The cell separation apparatus according to clause 2, wherein the liquid guiding groove is provided with a guiding tube connected with the collection tube.

12. The cell separation apparatus according to clause 1, wherein the liquid guiding groove is provided with a support column configured to support the cell separation component above the bottom of the tank and separate the cell separation component from the bottom of the tank.

13. The cell separation apparatus according to clause 12, wherein the support column is configured to be connected to the radial inner wall of the liquid guiding groove through a radial radiation arm.

14. The cell separation apparatus according to clause 12, wherein the support column is configured to extend downward from a bottom wall of the liquid guiding groove.

23. The cell separation apparatus according to clause 1, wherein the diameter of the blades is set to be smaller than an inner diameter of the cell separation component to provide an effect of tangential flow.

24. The cell separation apparatus according to clause 1, wherein a diameter of the blades is configured as 30%-45% of an inner diameter of the tank.

25. The cell separation apparatus according to clause 1, wherein a distance between a radial outermost point of the blades and a radial inner surface of the filter membrane is 1 mm-5 mm.

28. The cell separation apparatus according to clause 1, wherein the tangential flow driving component comprises: a central shaft; and a multi-layer paddle component, wherein the multi-layer paddle component is immersed in the mixture and includes an upper paddle component, an intermediate paddle component and a bottom paddle component arranged around the central shaft, the bottom paddle component being arranged close to the bottom of the tank and being driven by a driver outside the tank in a contactless manner, the intermediate paddle component being arranged between the upper paddle component, and the intermediate paddle component including a helical paddle.
29. The cell separation apparatus according to clause 28, wherein the bottom paddle component comprises a hub part and two or more inclined blades protruding from the hub part, wherein there is a gap between adjacent inclined blades in the circumferential direction.
31. The cell separation apparatus according to clause 29, wherein the hub part is provided with a pivot aperture in a center of its bottom wall, thereby being supported by a center column at the bottom of the tank and rotatable around the center column.
37. The cell separation apparatus according to clause 29, wherein the structures of the inclined blades are formed by a curved surface scanning on a curve of a side wall of the hub part, and the curve being a curve defined by a mathematical formula of a linear equation, a mathematical formula of a quadratic equation, or a mathematical formula of a cubic equation.
46. The cell separation apparatus according to clause 28, wherein a guiding cylinder is arranged in the tank and around the helical paddle, and the guiding cylinder is configured to cause the upward flowing mixture to be in a unidirectional laminar flow state.
48. The cell separation apparatus according to clause 28, wherein the helical paddle is arranged in an axial middle part inside the cell separation apparatus, and radially separated from the filter membrane by a small radial gap, wherein the radical gap ranges from 0.1 mm to 10 mm.
57. The cell separation apparatus of clause 28, wherein an axial distance between the upper paddle component and the intermediate paddle component is set to be greater than an axial distance between the intermediate paddle component and the bottom paddle component.
59. A bioreactor, comprising a cell separation apparatus and a tank used for containing a mixture of cells and a liquid, wherein the cell separation apparatus comprises: a cell separation component and a tangential flow driving component, wherein the cell separation component is arranged in a tank and immersed below a liquid level of the mixture and include a filter membrane and a liquid guiding groove, wherein the filter membrane is configured to filter the mixture and guide a separated liquid into the liquid guiding groove, the liquid guiding groove comprises a radial outer wall and a radial inner wall, and an internal cavity of the liquid guiding groove is only in fluid communication with the tank through one or more openings on the radial inner wall and through the filter membrane, or only in fluid communication with the tank through one or more openings on the radial outer wall and through the filter membrane; and the tangential flow driving component comprises one or more blades positioned radially inside the cell separation component and capable of rotating about a rotation shaft to drive the mixture to flow tangentially along the filter membrane.

Other features and advantages of the subject technology of the present disclosure would be described in the following description, and would be apparent in part from the description, or may be learned by practicing the subject technology of the present disclosure. The advantages of the subject technology of the present disclosure would be realized and obtained through the structure specially pointed out in the written description, the claims and the drawings.

It should be understood that both the foregoing general description and the following detailed description are exemplary and illustrative, and are intended to provide a further description of the subject technology of the present disclosure.

BRIEF DESCRIPTION OF THE DRAWINGS

After reading the specific implementation of the following drawings, it would better understand the multiple aspects of this disclosure, in the attachment.

DETAILED DESCRIPTION

Figure 1:
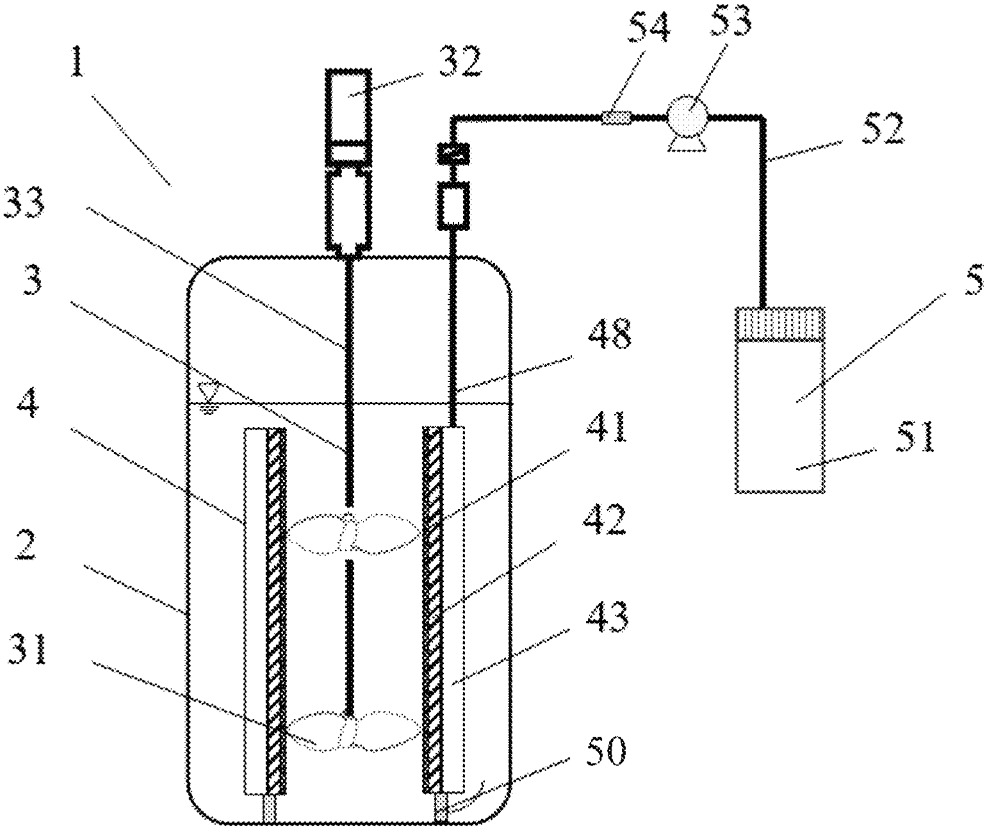
FIG. 1 is a schematic diagram of the cell separation apparatus of the present disclosure.

The following would be referred to the picture to describe the present disclosure, and the attachment shows several embodiments of this disclosure. However, it should be understood that the present disclosure can be presented in a variety of different ways, and it is not limited to the implementation example described below; In fact, the implementation example described below aims to make the disclosure more complete, and fully explain the scope of protection of the present disclosure to the technical personnel of the art. It should also be understood that the implementation examples of this article can be combined in various ways to provide more additional embodiments.

It should be understood that in all the attachments, the same attachment indicates the same components. In the attachment, for a clear time, the size of some characteristics can be deformed.

It should be understood that the use of words in the manual is only used to describe specific embodiments, and it is not designed to limit the present disclosure. All terms (including technical terms and scientific terms) used in the manual (including technical terms and scientific terms) have the meaning of the general understanding of technicians in the art. For simplicity and/or clarity, the functions or structures of public knowledge can no longer be explained in detail.

The single-number forms of the terms "one," "what," and "the should" are used to include plural forms unless clearly indicated. The use of the terms "including," "include," "containing," and "containing" represent the characteristics of the presence, but do not reject one or more other characteristics. The use of the terms "and/or" include any or more combinations of one or more in the relevant list. The terms use "between X and Y" and "between about X and Y" should be interpreted as including X and Y. The use of the term "between approximately X and Y" means "between about X and about Y", and the use of "from X to Y" means "from about X to about Y."

In the specification, when a component is described as located "on" another component, "attached" to another component, "connected" to another component "coupled" to another component, or "contacting" another component, etc., this component can be directly located on another component, attached to another component, connected to another component, or coupled to another component or contacting another element, and intermediate components can exist. In contrast, when a component is "directly" located "on" another component, "directly attached" to another component, "directly connected" to another component, "directly coupled" to another component or "directly contacting" another part, there would be no intermediate components. In the specification, one feature arrangement is "adjacent" to another feature, which can refer to one feature that has a part that overlaps with adjacent features or is located above or below the adjacent features.

In the specification, the use of "upper," "down," "left," "right," "front," "back," "high," "low," and other terms related to spatial relations can explain the relationship of one feature and another feature in the drawings. It should be understood that in addition to the orientation of the attached picture, the spatial relationship also includes the different orientations of the device in practical uses or operations. For example, when the device is inverted in the attached figure, it was originally described as the features of other features "below", and at this time, it can be described as "above" of other features. The device can also be directed in other ways (rotating 90 degrees or in other directions), and the relative spatial relationship would be explained accordingly.

FIG. 1 shows the cell separation apparatus 1 according to some embodiments of the present disclosure. The cell separation apparatus 1 is used for small disposable bioreactors. The disposable bioreactor includes a tank 2 to accommodate a mixture of cells and a medium, or a mixture of cells and other liquids. As shown in the figure, cell separation apparatus 1 includes a tangential flow driving component 3, a cell separation component 4, and a liquid collection component 5. The tangential flow driving component 3 and the cell separation component 4 can be placed in the bioreactor in the tank 2, and the liquid collection component 5 can be placed in the bioreactor and located outside the tank 2. The tangential flow driving component 3 is configured to drive the mixture of cells and the medium (or other liquids) flow circularly along the cell separation component 4 along a tangential direction; the cell separation component 4 is configured to separate the cells from the medium (or other liquids) during the cyclic flow of the mixture; and the liquid collection component 5 is used to collect the medium or other liquid separated from cells.

Figure 2:
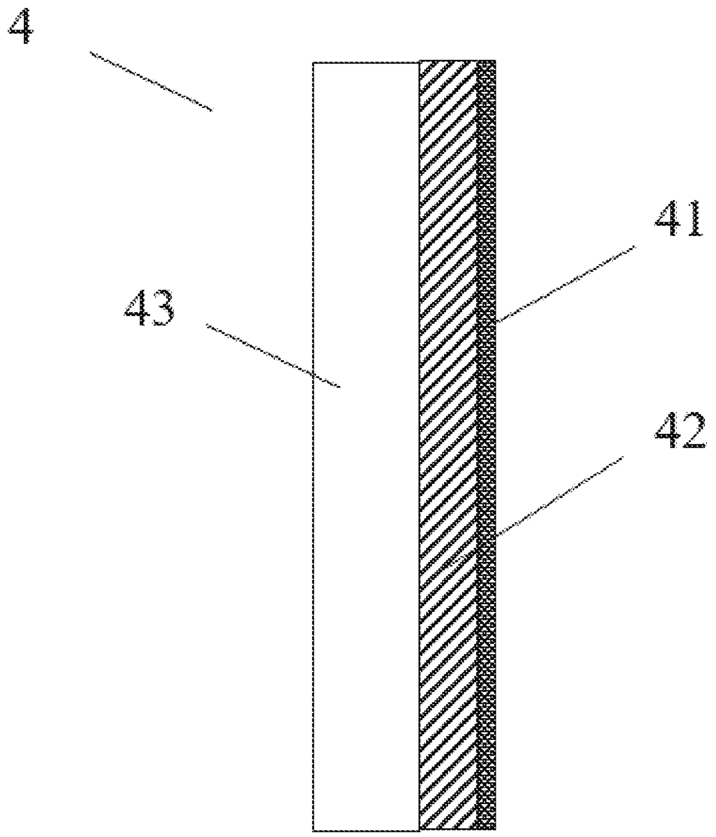
FIG. 2 is a local section view of the cell separation component of the cell separation apparatus shown in FIG. 1.
Figure 3:
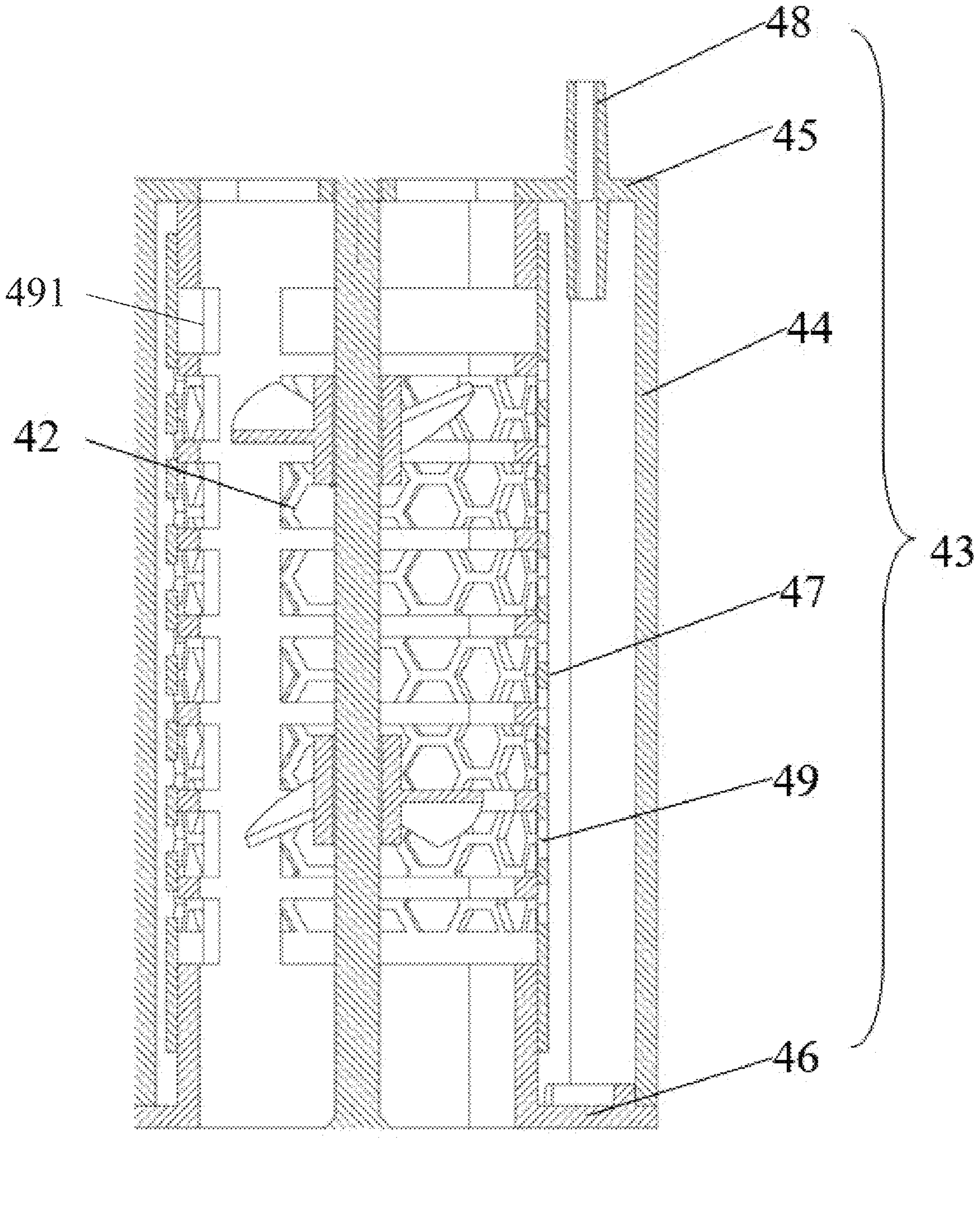
FIG. 3 is a section of cell separation components of the cell separation apparatus shown in FIG. 1.

The cell separation component 4 is placed in the tank 2, and the liquid surface of the mixture of the cell and the medium (or other liquid) is immersed. The cell separation component 4 is roughly a hollow cylinder, and includes a filter membrane 41, a support sheet 42, and a liquid guiding groove 43 that are adjacent and connected to each other, as illustrated in FIGS. 2 and 3. The filter membrane 41 is used to filter cells and the medium (or other liquids) mixtures. While blocking cells, the medium (or other liquid) flows to the liquid guiding groove 43 through the filtering film (or other liquid) while using the filter membrane 41. The support sheet 42 is used to support the filter membrane 41 to keep the filter membrane 41 flat. The liquid guiding groove 43 is used to accommodate the medium (or other liquid) of the filter membrane 41 and guide the medium to flow out of the tank 2.

As shown in FIG. 3, the liquid guiding groove 43 shows the middle empty tube and includes a radial outer wall 44 and a radial inner wall 47, and a top wall 45 and a bottom wall 46 extending between the radially outer wall 44 and the radially inner wall 47. The radial outer wall 44, the radial inner wall 47, the top wall 45 and the bottom wall 46 surround the internal cavity of the liquid guiding groove 43, and the internal cavity is only in fluid communication with the tank 2 through one or more openings 49 on the radial inner wall 47 and through the filter membrane 41.

The liquid guiding groove 43 also has a guiding tube 48 used for guiding the medium (or other liquid) contained in the liquid guiding groove 43 to flow out of the liquid guiding groove 43. The guiding tube 48 can extend vertically from the top wall 45 of the liquid guiding groove 43, such as extending to the liquid surface of the mixture of the cell and the medium (or other liquid).

The mixture of the medium (or other liquid) can circulate through the gap below the cell separation component 4. The support column 50 can extend down from the bottom wall 46 of the liquid guiding groove 43. In other embodiments, the support column 50 may be located in the hollow tube of the liquid guiding groove 43, and is connected by the radial inner wall 47 of the radial drainage slot 43 from the radial inner wall 47 from its radial radiation arm 491. In some embodiments, the height design of the support column 50 makes the gap between the cell separation component 4 and the tank 2 as small as possible, so as not to cause turbulence to affect cell growth.

The filter membrane 41 can be made of PCTE, PETE, PTFE, PP, PC, Nylon, PES or sintered porous materials. The filter membrane 41 is treated with hydrophilic and positive charge or negative charge, so it is not easy to be adsorbed by cells to block the filter membrane. The filter membrane 41 Followed by biotechnology (such as stem cells, tumor cells, CHO cells, or microcarriers, etc.), a variety of pore diameters can be used (including about 5 μm, about 10 μm, about 20 μm, about 50 μm, about 100 μm, about 200 μm, etc.)

Figure 4:
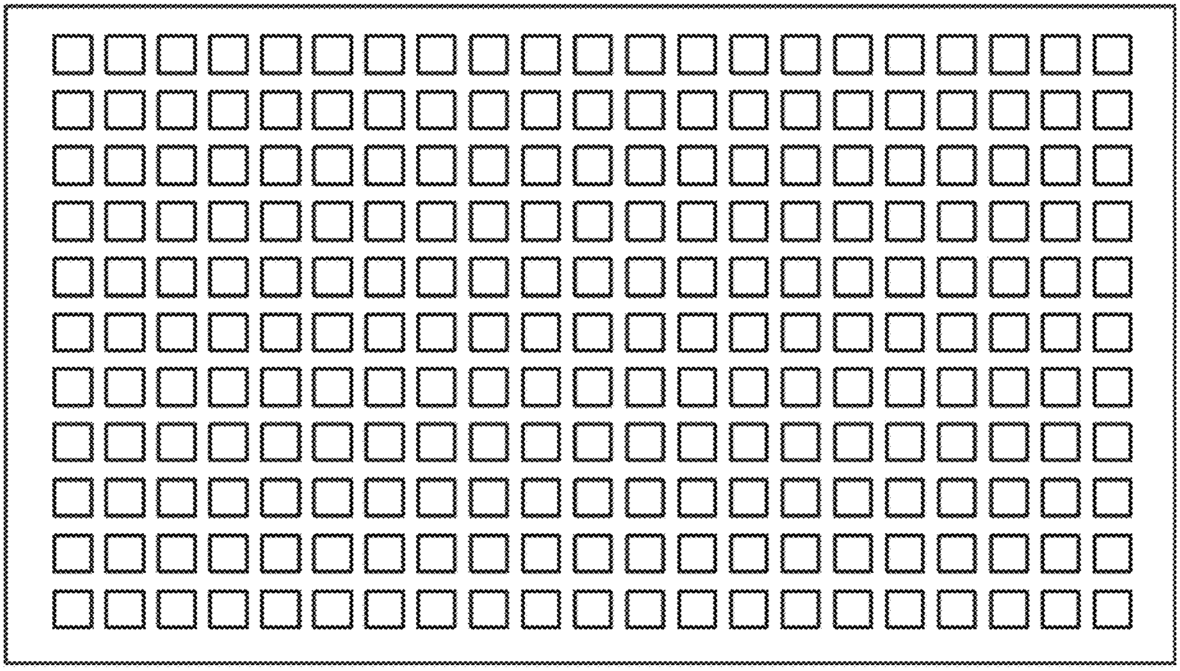
FIG. 4 and FIG. 5 are schematic diagrams of support sheets of the cell separation apparatus shown in FIG. 1.
Figure 5:
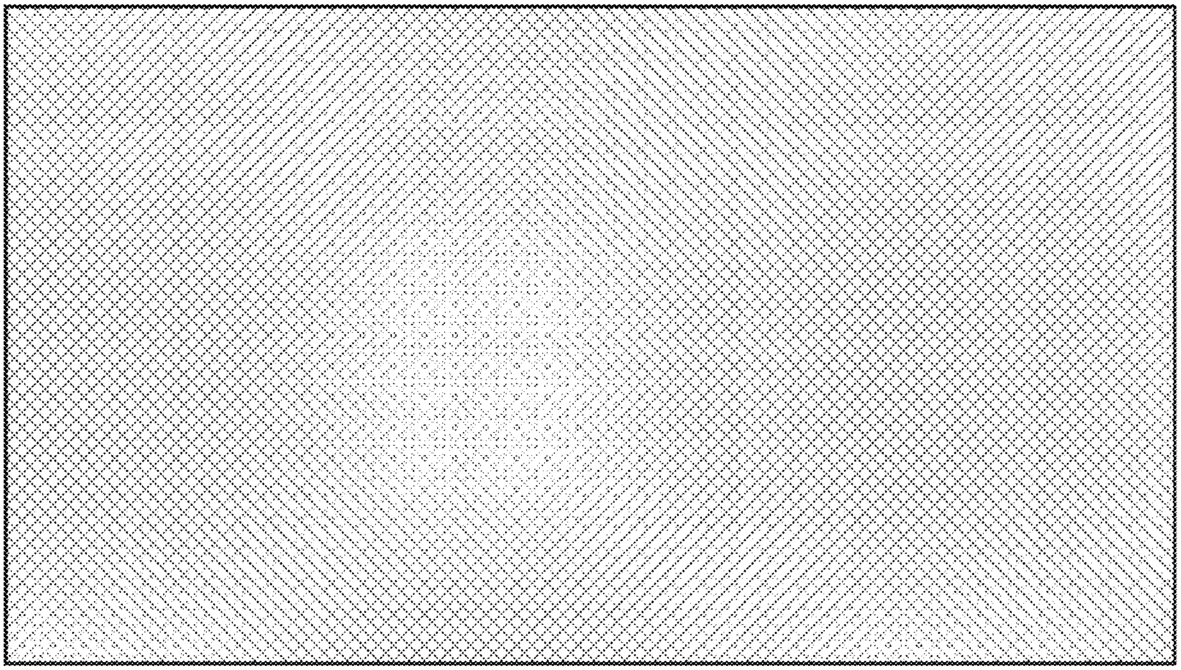

The support sheet 42 can be made of punching soft materials (e.g., soft glue material), as shown in FIG. 4. The shape of the holes can be roughly circular, general square, rough hexagonal, or any other shape. In some embodiments, the support sheet 42 can also be made of fiber porous materials, as shown in FIG. 5. The thickness of the support sheet 42 can be between about 50 μm-about 300 μm.

The filter membrane 41 is fixed to the support sheet 42 by means of hot melting, cohesion, laser welding, etc., and the support sheet 42 is connected to the radial inner wall 47 of the liquid guiding groove 43 by means of hot melting, concave convex fitting, laser welding, etc.

In some embodiments, the radial outer wall 44, the radial inner wall 47, the top wall 45, and the bottom wall 46 of the liquid guiding groove 43 surround the internal cavity of the liquid guiding groove 43, and the inner cavity is only in fluid communication with the tank 2 through one or more openings on the radial outer wall 44 (rather than the radial inner wall 47) and through the filter membrane 41. The filter membrane 41 is fixed to the support sheet 42 by means of hot melting, cohesion, laser welding, etc., and the support sheet 42 is connected to the radial outer wall 44 of the liquid guiding groove 43 by means of hot melting, concave convex fitting, laser welding, etc.

The tangential flow driving component 3 includes one or more blades 31 and a motor 32 for driving blade(s) 31. In some embodiments, the tangential flow driving component 3 is also referred to as a stirring system (e.g., the stirring system 60 shown in FIG. 6). The blade 31 is placed in the tank 2 and is immersed in a mixture of cells and the medium (or other liquids). The blade 31 may be located in the radial interior of the cell separation component 4 and rotate around the rotation shaft 33 to drive the mixture of cells and culture medium (or other liquid) to circulate tangentially (i.e., vertical direction) along the inner and outer surfaces (for example, including filter membrane 41, radial outer wall 44, radial inner wall 47 of liquid guiding groove 43, etc.) of the cell separation component 4. The rotation of blade 31 would not cause too high shear force, so it would not cause damage to animal cells. The motor 32 is placed outside the tank 2, and its driving shaft is directly connected to the rotation shaft 33 of the blade 31, or the rotation shaft 33 of the blade 31 is connected through the speed adjustment mechanism such as the gearbox to drive the rotation shaft 33 and the blade 31 to rotate. In some embodiments, the rotation shaft 33 is also referred to as a central shaft. More details regarding the tangential flow driving component 3 may be found elsewhere in the specification, e.g., in FIGS. 6-11 and descriptions thereof.

The motor 32 may be connected to the controller (not shown). The output power of the motor 32 is one of the key design parameters. The larger the output power of the motor 32, the greater the flowing speed of the mixture, and the longer the service life of the filter membrane 41. Especially in the case of high-density cell culture, increasing the increase in flowing speed can reduce the blockage speed of the filter membrane 41.

The distance between the blades 31 and the filter membrane 41 is also one of the key design parameters. The closer the distance, the higher the velocity of the liquid in the mixture passing through the filter membrane 41, but it would also significantly increase the local shear force of the liquid, which would affect the physiological characteristics of stem cells. The diameter of the blades 31 is set to be less than the inner diameter of the filter membrane 41 (for example, the distance between the radial most of the radial blades 31 and the radial surface of the filter membrane 41 is about 1 mm-about 5 mm), provide the flowing effect of tangential flow in a small space. In some embodiments, the diameter of the blades 31 can be designed into about 30%-45% of the inner diameter of the tank. The blades 31 can be used in the form of a complete axis, such as single-layer or multi-layer elephant ear blades, marine blades and helical blades.

The liquid collection component 5 is placed outside the tank 2. The liquid collection component 5 includes collection container 51 and collection tube 52. The collection tube 52 is connected to the collection container 51, and the other end is connected to the guiding tube 48 to the liquid derivatives 43 to guide the medium (or other liquid) of the liquid derivative groove 43 to the collection container 51. In some embodiments, the collection tube 52 can be flexible, so that the collection container 51 can be placed in any appropriate location outside the tank 2. A pump 53 (such as peristaltic pump, etc.) may be set on the collection pipe 52 and connected to the controller to help the medium (or other liquid) pump and pump to the collection container 51. The controller can change the pump speed change of the pump 53 of the signal control pump 53 according to the process requirements, the pump speed of the other replenishment pump, the weight of the pump, or some sensors (such as the living cell sensor) to adjust the drainage rate.

In some embodiments, the pressure sensor 54 connected to the controller can be set on the collection tube 52 to monitor the liquid pressure in the collection tube 52. When the pressure sensor 54 detects the cell blocking the filter membrane 41 and the pressure in the collection tube 52 rises, the controller stops the work of the pump 53 and sends the alarm signal to the operator.

The operation method of the cell separation apparatus 1 is introduced below. First, put the bioreactor into the ultra-net platform for adding the medium and for inoculation, and then place the bioreactor to the console, and connect the corresponding sensor. The controller sends a start signal to the motor 32, and the motor 32 drives the blades 31 to rotate around the rotation shaft 33, thereby driving the mixture of cells and culture medium (or other liquids) to circulate in a tangential (i.e., vertical) direction along the inner and outer surfaces (including, for example, the filter membrane 41, the radial outer wall 44 of the liquid guiding groove 43, the radial inner wall 47, etc.) of the cell separation component 4. When you need to change the liquid, clean these components, or separate cells or microcarriers, the controller starts the pump 53. The pumping effect generated by the pump 53 enables the medium (or other liquid) to separate the cells from the liquid in filter membrane 41 and enter the liquid guiding groove 43, and then enter the collection container 51 by collection tube 52.

After discharging a certain volume of abandoned medium from the tank 2, the pump 53 can reverse the operation, so that the liquid in the collection tube 52 can flow reversely and rush to the filter membrane sheet 41 to prevent the cells from blocking the filter membrane 41.

The cell separation apparatus 1 according to the embodiments of the present disclosure uses the blades 31 to drive the mixture, so that a low shear force can be achieved and the cells are not affected.

In addition, the cell separation apparatus 1 according to the embodiments of the present disclosure filter the mixture through the tangential flow of the mixture along the filter membrane, so that the filter membrane is not easily blocked and can be used for a long time.

Figure 6:
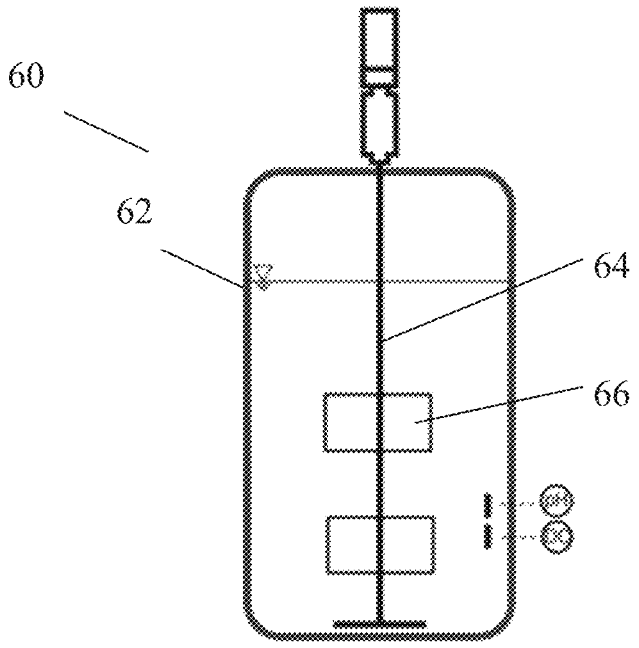
FIG. 6 is a schematic diagram of the use environment of the stirring system according to the embodiment of the present disclosure.

FIG. 6 shows a schematic diagram of a stirring system 60 according to an embodiment of the present disclosure. The stirring system 60 is applicable to various bioreactors, especially bioreactors of animal cells (such as stem cells and T cells). The bioreactor includes a tank 62 used for containing or accommodating a mixture of cells, microcarriers and culture media, or a mixture of cells, microcarriers and other liquids. In some embodiments, the stirring system 60 may be configured to mix contents in the tank 62, such as cells and the liquid (e.g., culture medium).

In some embodiments, the stirring system 60 may be a part of a cell separation apparatus. Merely by way of example, the stirring system 60 may be implemented as the tangential flow driving component 3 of the cell separation apparatus 1 shown in FIG. 1. In this case, the stirring system 60 may be further configured to provide a tangential force to cause the mixture of cells and the culture medium to flow in a limited space (e.g., within the cell separation apparatus 1), so that the cells and the liquid may be separated by the filter membrane 41. The separated liquid may be collected by the collection container 51 through the collection tube 52, as shown in FIG. 1.

As shown in the figure, the stirring system 60 includes a central shaft 64 and a multi-layer paddle component 66 arranged around the central shaft 64. The multi-layer paddle component 66 is immersed in a mixture of cells, microcarriers, and culture media (or other liquids). The multi-layer paddle component 66 may form a large upward thrust on the mixture at a lower speed to form an upstream flow field in the tank 62, thereby improving the suspension capacity of the microcarrier and the cells attached to the microcarrier.

The multi-layer paddle component 66 may be a three-layer paddle component, a four-layer paddle component, or a paddle component including more layers. Each layer of the paddle component can be set to be the same or different from each other. Taking the three-layer paddle component as an example, the structure of the multi-layer paddle component 66 of the stirring system 60 according to the embodiment of the present disclosure is described below.

Figure 7A:
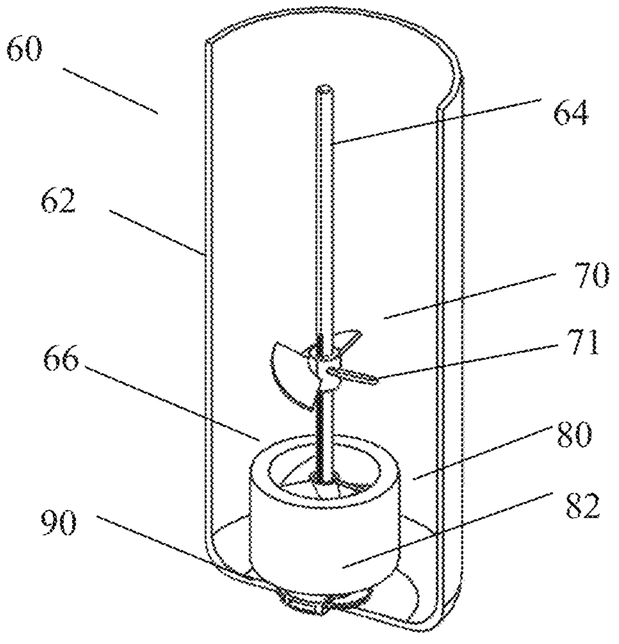
FIGS. 7A and 7B are perspective and front views of a stirring system according to an embodiment of the present disclosure.
Figure 7B:
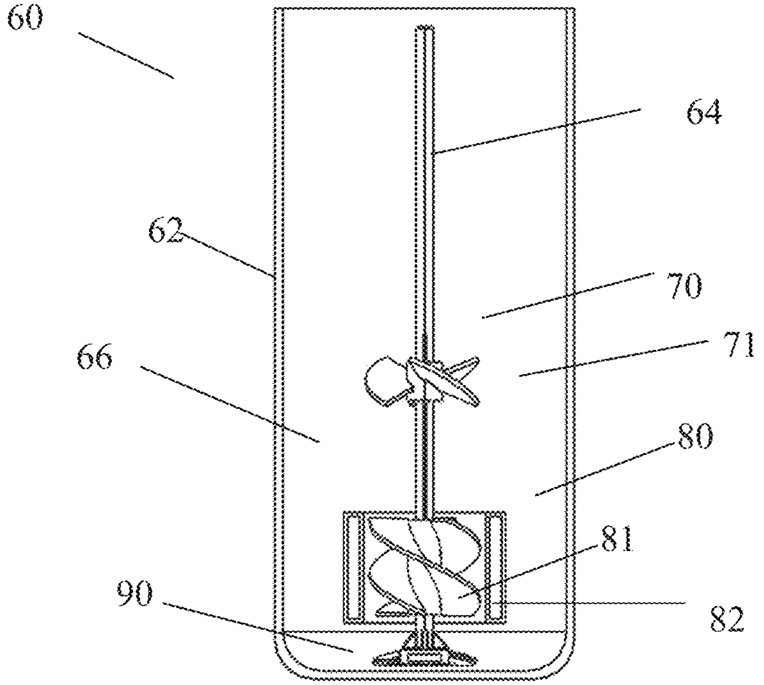

FIGS. 7A and 7B show a perspective view and a front view of the stirring system 60, respectively. As shown in the figure, the multi-layer paddle component 66 includes an upper paddle component 70, an intermediate paddle component 80, and a bottom paddle component 90. The upper paddle component 70, the intermediate paddle component 80, and the bottom paddle component 90 are arranged around the central shaft 64 and are immersed in a mixture of cells, microcarriers, and culture media (or other liquids). The upper paddle component 70 is arranged at the upper part of the tank 62, the bottom paddle component 90 is arranged close to the bottom of the tank 62, and the intermediate paddle component 80 is arranged between the upper paddle component 70 and the bottom paddle component 90. The axial distance between the upper paddle component 70 and the intermediate paddle component 80 and the axial distance between the intermediate paddle component 80 and the bottom paddle component 90 can be set to be the same or different from each other. In some embodiments, the axial distance between the upper paddle component 70 and the intermediate paddle component 80 may be set to be greater than the axial distance between the intermediate paddle component 80 and the bottom paddle component 90.

Figure 8A:
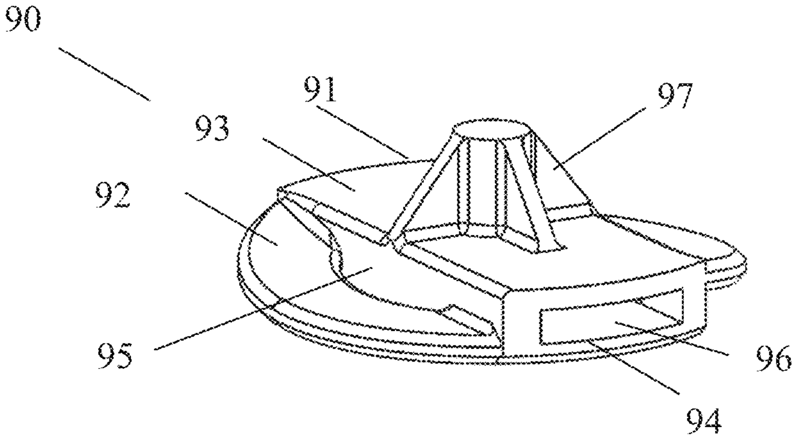
FIGS. 8A and 8B are perspective and front views of the bottom paddle component of the stirring system shown in FIGS. 7A and 7B.
Figure 8B:
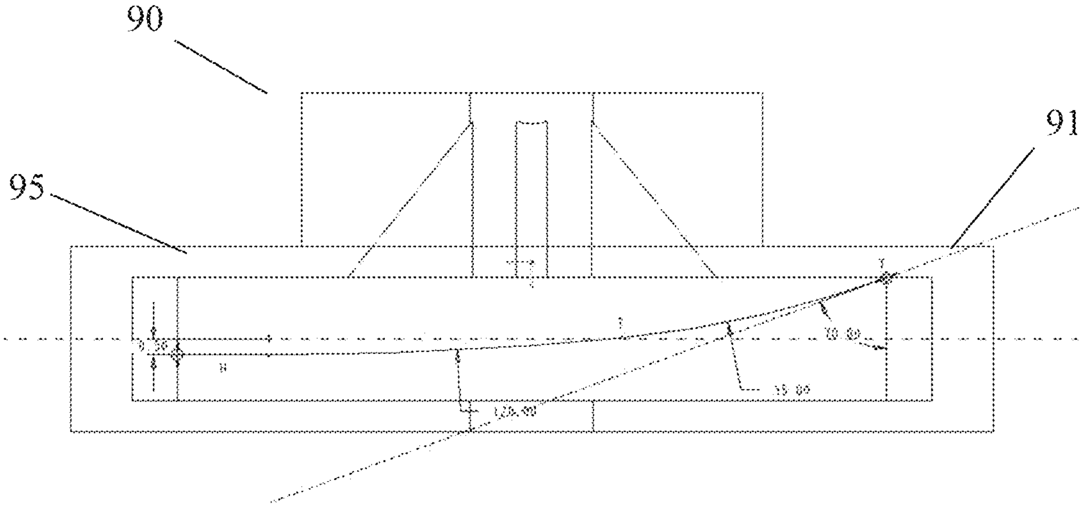

FIGS. 8A and 8B show a perspective view and a front view of the bottom paddle component 90, respectively. As shown in the figure, the bottom paddle component 90 is used to transport particles such as microcarriers and/or cells at the bottom of the tank 62 to the upper paddle component. The bottom paddle component 90 includes a hub part 91 and two or more inclined blades 92 extending from the hub part 91 along a radial direction. The hub part 91 is in a flat disk shape, and the cross section can be circular, elliptical, triangular, quadrilateral, or other polygons, which can include straight sides or curved sides.

The hub part 91 includes a top wall 93, a bottom wall 94, and a side wall 95 connecting the top wall 93 and the bottom wall 94. The top wall 93, the bottom wall 94, and the side wall 95 surround the middle cavity 96 of the hub part 91. The center of the top wall 93 of the hub part 91 is fixed to the bottom end of the central shaft 64, so that the hub part 91 can rotate together with the central shaft 64, and the top end of the central shaft 64 can be rotatably supported by the top cover of the tank 62. In some embodiments, the connecting portion between the hub part 91 and the central shaft 64 may be reinforced by a reinforcing rib 97. The bottom wall 94 of the hub part 91 is provided with a pivot aperture in its center, so that it can be supported on the center column at the bottom of the tank 62 and rotate around the center column at the bottom of the tank 62. The middle cavity 96 of the hub part 91 houses a magnet. The magnet can be magnetically coupled with a driver (such as a magnetic stirrer) outside the tank 62, so that the driver can drive the entire multi-layer paddle component 66 to rotate around the central shaft 64. The combination of magnet and driver provides driving power for the stirring system 60 in a contactless way, avoiding the problems of liquid leakage or microbial pollution in the contact drive mechanism arrangement scheme (such as the scheme of motor driving central shaft, etc.).

The inclined blade 92 is fixed to the side wall 95 of the hub part 91 and extends radially outward from the side wall 95. The number of inclined blades 92 can be set to 2, 3, or more. The inclined blades 92 may be arranged to be evenly distributed in a circumferential direction around the hub part 91. The inclined blades 92 is structured by scanning a curve surface on a curve of a side wall 95 of the hub part 91. Specifically, a straight line (corresponding to the width of the blade) perpendicular to the outer surface of the side wall 95 of the hub part 91 is moved along the curve drawn on the side wall 95 of the hub part 91 from one end of the curve to the other end of the curve to form the inclined blade 92. FIG. 8B shows a curve drawing method of inclined blades 92. The method is to ensure that the lower starting point on the left side of the curve is located in the lower part of the hub part 91, and the upper end point on the right side of the curve is located in the upper part of the hub part 91. The curve at the lower starting point is tangent to the horizontal line, and the curve at the upper end point maintains a certain angle with the horizontal line; The natural transition of the curve is ensured through the control of 2-3 points between the lower starting point and the upper ending point. The inclined blades 92 can also use other curve drawing methods, such as the linear drawing method, the spiral line drawing method, or any other linear equation, the secondary equation, and the three equations.

Since the inclined blade 92 is close to the bottom of the tank 62, the dead zone (i.e., an area in which the mixture stops flowing) below the inclined blades 92 can be reduced as much as possible by reducing the paddle area of the inclined blades 92. Alternatively, a part of the volume may be left between adjacent inclined blades 92, or there may be a gap in the circumferential direction, so as to maintain the mixing effect and reduce the dead zone under the paddle as much as possible.

The bottom paddle component 90 adopts a unique combination of the hub part 91 and the inclined blades 92 fixed to the side wall of the hub part 91. The hub part 91 adopts a flat disc body, and the height of the inclined blades 92 is less than or equal to the height of the hub part 91, so the height of the whole combination may be set to be small. The bottom paddle component 90 can be located as low as possible in the bioreactor tank 62 to provide power in the bottom environment of the tank 62 to transport the microcarriers or cells at the bottom of the tank 62 to the upper paddle component, thereby strengthening the continuous suspension capacity of the microcarriers or cells at the bottom of the tank 62.

Figure 9A:
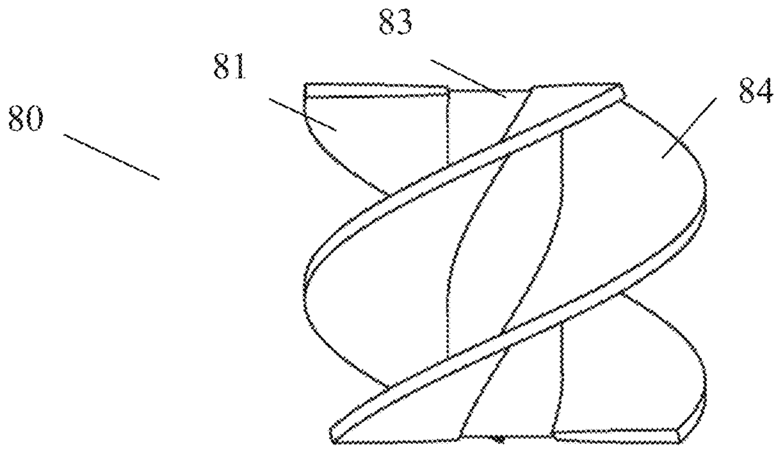
FIG. 9A is a front view of the intermediate paddle component of the stirring system shown in FIGS. 7A and 7B.

FIG. 9A shows a front view of the intermediate paddle component 80. As shown in the figure, the intermediate paddle component 80 is used to directionally push particles such as microcarriers or cells stirred by the bottom paddle component 90 into the ascending channel. The intermediate paddle component 80 includes a helical paddles 81 surrounding the central shaft 64, and the helical paddles 81 has a cylindrical hub part 83 and helical blades 84 surrounding the hub part 83.

Figure 9B:
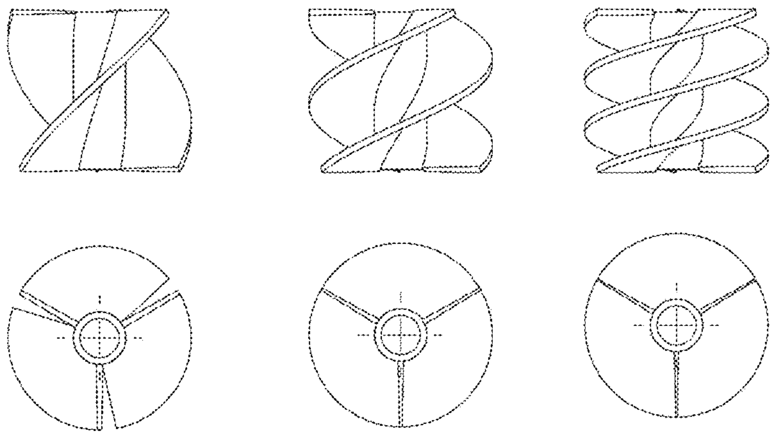
FIG. 9B is a multiple variant design of the intermediate paddle component.

The number of helical blades 84 can be set to 2, 3, or more. The helical blades 84 may be arranged to be uniformly distributed in a circumferential direction around the central shaft 64. The helical blade 84 is formed by scanning the curved surface of the spiral line drawn on the side wall of the hub part 83. Specifically, the helical blade 84 is formed by moving a straight line (corresponding to the width of the paddle) perpendicular to the outer surface of the side wall of the hub part 83 along the helix drawn on the side wall of the hub part 83 from one end of the helix to the other end of the helix. The spiral takes the cross-sectional circle of the hub part 83 as the diameter and the height of the hub part 83 as the height, and the variable pitch and number of turns of the spiral ensure that the helical blades 84 and the hub part 83 are at the same height. As shown in FIG. 9B, the pitch and number of revolutions of each helical blade 84 can be determined according to actual needs, and the difference it brings is the difference between speed and pumping flow. In some embodiments, the intermediate paddle component 80 may also include a plurality of helical paddles 81, and these helical paddles 81 may be axially distributed along the central shaft 64.

Returning to FIGS. 7A and 7B, a guiding cylinder 82 can be arranged in the tank 62, and the guiding cylinder 82 surrounds the helical paddles 81. The guiding cylinder 82 is used to guide the upward flowing mixture, so that the upward flowing mixture will not converge with the reflux mixture, so as to ensure that the upward flowing mixture is in a unidirectional laminar flow state, which is very important for microcarriers or single suspended cells.

The guiding cylinder 82 is used to guide the upward flowing mixture, so that the upward flowing mixture will not converge with the reflux mixture, so as to ensure that the upward flowing mixture is in a unidirectional laminar flow state, which is very important for microcarriers or single suspended cells. The cell separation apparatus is in the shape of a hollow cylinder, and has a filter element for filtering cells in its radial interior. The helical paddles 81 can be arranged in the axial middle part inside the cell separation apparatus, and is radially separated from the filter element by a small gap. Due to the narrow radial gap between the helical paddles 81 and the filter element, the clockwise or counterclockwise rotation of the helical paddles 81 will produce a pulse vortex in the narrow radial gap, which can remove the cells attached to the filter element. The radial clearance between the helical paddles 81 and the filter element ranges from 0.1 mm to 10 mm, and the size is related to the volume and diameter of the tank 62. If the radial clearance increases, the damage caused by shear force to cells decreases, but the eddy energy formed decreases, so the ability to remove cell blockers on the filter element decreases; On the contrary, if the radial gap is reduced, the shear force damage to cells is significantly increased, but the energy of vortex formation is increased, so the ability to remove cell blockers on the filter element is increased. Therefore, the determination of the gap size is one of the core parameters of the stirring system 60. Depending on the type, shape, diameter and density of cells in the bioreactor, the helical paddles 81 can have a variety of deformations, such as the increase of paddle pitch, the increase of the number of paddles, and so on. These increases will increase the flow of the filter element of the cell separation apparatus and change the fluid velocity, thus affecting the filtration flow.

In some embodiments, the filter element may include a filter membrane (e.g., the filter membrane 41 shown in FIG. 1). The filter membrane may be made of one or more appropriate materials for separating cells. For example, the filter membrane may be made of PTFE, PP, PC, nylon, PES or sintered porous material.

In some embodiments, the gas distributor may be arranged between the bottom paddle component 90 and the intermediate paddle component 80 and used to provide gas in the form of bubbles to the cells in the tank 62. The design of the helical paddles 81 of the intermediate paddle component 80 and the guiding cylinder 82 enhances the mass transfer of bubbles in the guiding cylinder 82, and bubbles can provide assistance for the suspension of particles such as microcarriers.

FIGS. 7A and 7B also show a perspective view and a front view of the upper paddle component 70. As shown in the figure, the upper paddle component 70 is arranged on the upper part of the liquid of the tank 62 and is mainly used to provide mixing. The upper paddle component 70 may include an i having a hub part and paddles surrounding the hub part. The inclined paddle 71 generally include three blades, and can also include two to six blades. In the top view, the blades of the inclined paddle 71 do not overlap or overlap a little, and the coverage area is the circle of the entire diameter, and the center of the paddle can be located on the hub part. The inclination angle of the paddle of the inclined paddle 71 is generally 30°, 45° or 60°. The sharp angle of paddles of inclined paddle 71 is generally chamfered to reduce the shear force or the extreme value of speed. Depending on the angle of the paddle in the clockwise direction, the inclined paddle 71 may drive the fluid upward or downward. In some embodiments, the upper paddle component 70 may also include a plurality of inclined paddle 71, and these inclined paddles 71 may be axially distributed along the central shaft 64.

Compared with the traditional stirring system of the bioreactor, the bottom paddle component 90 and the intermediate paddle component 80 of the stirring system 60 according to the present disclosure are closer to the bottom of the tank 62. The bottom paddle component 90 is 2 mm-10 mm away from the bottom of the tank 62, while the intermediate paddle component 80 and the guiding cylinder 82 are close to the bottom paddle component 90, so that the suspended particles can be effectively sucked into the middle layer guide area. This design can effectively ensure that the stirring system in the bioreactor may also keep particles such as microcarriers or cells suspended at a low speed. The diameters of the upper paddle component 70 and the intermediate paddle component 80 are set to be approximately the same, and are 0.4-0.6 times the inner diameter of the tank 62. The upper paddle component 70 is usually designed to be approximately 1.0-1.5 times the diameter from the intermediate paddle component 80, which mainly provides mixing.

Figure 10A:
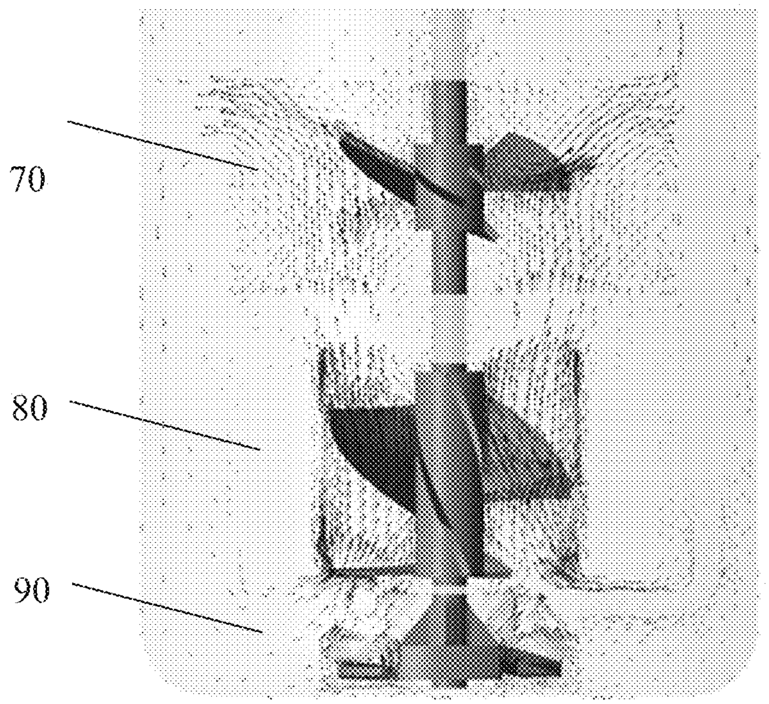
FIGS. 10A and 10B are the flow field velocity vector diagrams of the stirring system shown in FIGS. 7A and 7B.
Figure 10B:
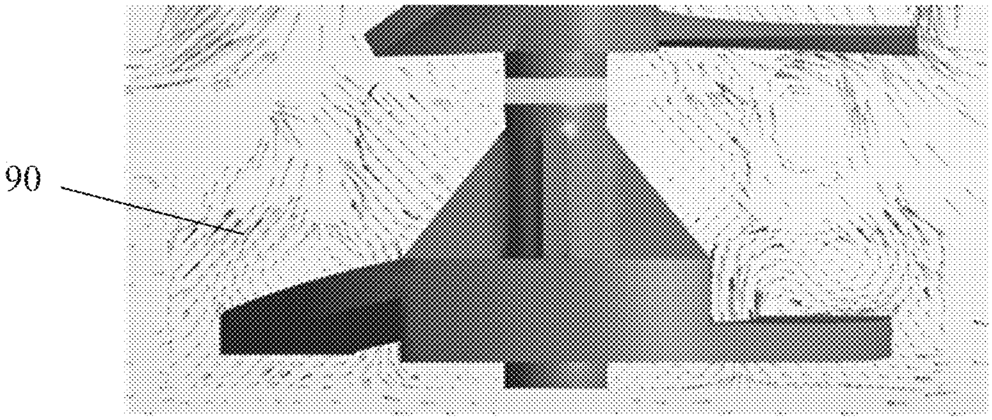

FIGS. 10A and 10B show the velocity vector diagram of the flow field driven by the computer simulated stirring system 60. It can be seen from FIG. 10A that the stirring system 60 forms a good liquid circulation in the tank 62 of the bioreactor. The bottom paddle component 90 and the intermediate paddle component 80 regulate the flow state of the liquid to form a laminar flow in a single direction; the upper paddle component 70 has a good mixing effect on the liquid lifted by the lower paddle component. As can be seen from FIG. 10B, the bottom paddle component 90 forms an upward flowing fluid state, which may support the continuous suspension of the microcarrier, and has a good effect on improving the flow field at the bottom of tank 62.

Figure 11:
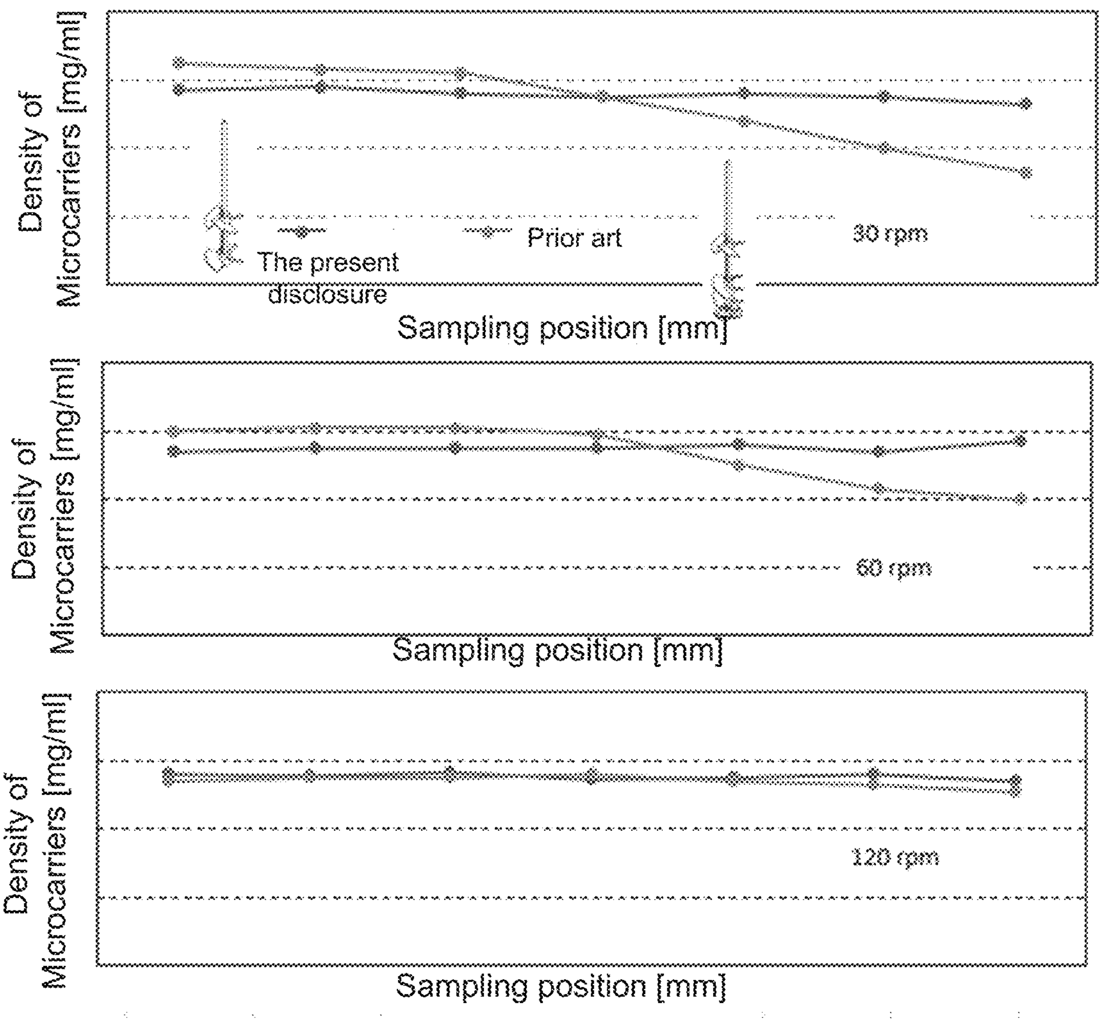
FIG. 11 shows experimental results of the performance comparison between the stirring system shown in FIGS. 7A and 7B and the traditional double-layer elephant ear paddle.

FIG. 11 shows the performance comparison experiment of the stirring system 60 according to the present disclosure and the traditional double-layer Elephant Ear paddle at different speeds. The slurry diameter ratio of stirring system 60 is consistent with that of traditional double-layer Elephant ear blades, both of which are 0.45; the concentration of the microcarrier is obtained by sampling along the axial direction of the tank 62. The abscissa in FIG. 11 represents the sampling position along the axial direction of tank 62, and the ordinate represents the concentration of microcarriers. It can be seen from the figure that the microcarrier suspension capacity of the traditional double-layer Elephant ear blades at low speed is not ideal, and the minimum speed for suspending the microcarrier is between 90 rpm and 120 rpm, while the minimum speed can be effectively reduced to 30 rpm according to the stirring system 60 of the present disclosure. Therefore, according to the disclosed stirring system 60, it can provide sufficient lift at a low speed to continuously suspend microcarriers, but also reduce the damage to animal cells as much as possible.

In addition, the stirring system 60 according to the present disclosure can effectively remove the cells attached to the filter element and is not easy to block the filter element, thereby ensuring the long-term use of the cell separation apparatus.

Although the present disclosure embodiments have been described, the technical personnel of the art should understand that in the case of essentially not separated from the spirit and scope of the present disclosure, multiple changes can be made on the present disclosure demonstration embodiments. Therefore, all changes and changes are included within the scope of the present disclosure limited by claims, the present disclosure is limited by additional claims, and equivalent of these claims is also included.

We claim:

1. A cell separation apparatus for a bioreactor comprising a tank for containing a mixture of cells and a liquid, wherein the cell separation apparatus comprises: a cell separation component and a tangential flow driving component, wherein the cell separation component is arranged in a tank and immersed below a liquid level of the mixture and include a filter membrane and a liquid guiding groove, wherein the filter membrane is configured to filter the mixture and guide a separated liquid into the liquid guiding groove, the liquid guiding groove comprises a radial outer wall and a radial inner wall, and an internal cavity of the liquid guiding groove is only in fluid communication with the tank through one or more openings on the radial inner wall and through the filter membrane, or only in fluid communication with the tank through one or more openings on the radial outer wall and through the filter membrane; and the tangential flow driving component comprises one or more blades positioned radially inside the cell separation component and capable of rotating about a rotation shaft to drive the mixture to flow tangentially along the filter membrane.

2. The cell separation apparatus according to claim 1, further comprising a liquid collection component arranged outside the tank, the liquid collection component comprising a collection container in fluid communication with the liquid guiding groove, and a collection tube in fluid communication with the collection container and the liquid guiding groove.

3. The cell separation apparatus according to claim 2, wherein a pump is disposed on the collection tube, and the separated liquid is pumped from the liquid guiding groove to the collection container.

4. The cell separation apparatus according to claim 2, wherein a pressure sensor is disposed in the collection tube to monitor a liquid pressure in the collection tube.

5. The cell separation apparatus according to claim 2, wherein the liquid guiding groove is provided with a guiding tube connected with the collection tube.

6. The cell separation apparatus according to claim 1, wherein the cell separation component further comprises a support sheet positioned between the liquid guiding groove and the filter membrane, and the support sheet is configured to support the filter membrane.

7. The cell separation apparatus according to claim 1, wherein the liquid guiding groove is provided with a support column configured to support the cell separation component above the bottom of the tank and separate the cell separation component from the bottom of the tank.

8. The cell separation apparatus according to claim 7, wherein the support column is configured to be connected to the radial inner wall of the liquid guiding groove through a radial radiation arm.

9. The cell separation apparatus according to claim 7, wherein the support column is configured to extend downward from a bottom wall of the liquid guiding groove.

10. The cell separation apparatus according to claim 1, wherein the diameter of the blades is set to be smaller than an inner diameter of the cell separation component to provide an effect of tangential flow.

11. The cell separation apparatus according to claim 1, wherein a diameter of the blades is configured as 30%-45% of an inner diameter of the tank.

12. The cell separation apparatus according to claim 1, wherein a distance between a radial outermost point of the blades and a radial inner surface of the filter membrane is 1 mm-5 mm.

13. The cell separation apparatus according to claim 1, wherein the tangential flow driving component comprises:

a central shaft; and a multi-layer paddle component, wherein the multi-layer paddle component is immersed in the mixture and includes an upper paddle component, an intermediate paddle component and a bottom paddle component arranged around the central shaft, the bottom paddle component being arranged close to the bottom of the tank and being driven by a driver outside the tank in a contactless manner, the intermediate paddle component being arranged between the upper paddle component and the bottom paddle component and including a helical paddle.

14. The cell separation apparatus according to claim 13, wherein the bottom paddle component comprises a hub part and two or more inclined blades protruding from the hub part, wherein there is a gap between adjacent inclined blades in the circumferential direction.

15. The cell separation apparatus according to claim 14, wherein the hub part is provided with a pivot aperture in a center of its bottom wall, thereby being supported by a center column at the bottom of the tank and rotatable around the center column.

16. The cell separation apparatus according to claim 14, wherein the structures of the inclined blades are formed by a curved surface scanning on a curve of a side wall of the hub part, and the curve being a curve defined by a mathematical formula of a linear equation, a mathematical formula of a quadratic equation, or a mathematical formula of a cubic equation.

17. The cell separation apparatus according to claim 13, wherein a guiding cylinder is arranged in the tank and around the helical paddle, and the guiding cylinder is configured to cause an upward flowing mixture to be in a unidirectional laminar flow state.

18. The cell separation apparatus according to claim 13, wherein the helical paddle is arranged in an axial middle part inside the cell separation apparatus, and radially separated from the filter membrane by a small radial gap, wherein the radical gap ranges from 0.1 mm to 10 mm.

19. The cell separation apparatus of claim 13, wherein an axial distance between the upper paddle component and the intermediate paddle component is set to be greater than an axial distance between the intermediate paddle component and the bottom paddle component.

20. A bioreactor, comprising a cell separation apparatus and a tank used for containing a mixture of cells and a liquid, wherein the cell separation apparatus comprises: a cell separation component and a tangential flow driving component, wherein the cell separation component is arranged in a tank and immersed below a liquid level of the mixture and include a filter membrane and a liquid guiding groove, wherein the filter membrane is configured to filter the mixture and guide a separated liquid into the liquid guiding groove, the liquid guiding groove comprises a radial outer wall and a radial inner wall, and an internal cavity of the liquid guiding groove is only in fluid communication with the tank through one or more openings on the radial inner wall and through the filter membrane, or only in fluid communication with the tank through one or more openings on the radial outer wall and through the filter membrane; and the tangential flow driving component comprises one or more blades positioned radially inside the cell separation component and capable of rotating about a rotation shaft to drive the mixture to flow tangentially along the filter membrane.

* * * * *